United States Patent
Galusha et al.

(10) Patent No.: US 12,430,599 B2
(45) Date of Patent: Sep. 30, 2025

(54) MEDICAL LIABILITY PREVENTION, MITIGATION, AND RISK QUANTIFICATION

(71) Applicant: Aon Risk Consultants, Inc., Chicago, IL (US)

(72) Inventors: Larry Joe Galusha, Grosse Ile, MI (US); Jasmine Gilbert, Tampa, FL (US); Kelly M. Black, Houston, TX (US); Tim Davidson, Franklin, TN (US); Peter Berardinucci, Hatfield, PA (US)

(73) Assignee: AON RISK CONSULTANTS, INC., Chicago, IL (US)

( * ) Notice: Subject to any disclaimer, the term of this patent is extended or adjusted under 35 U.S.C. 154(b) by 114 days.

(21) Appl. No.: 18/236,816

(22) Filed: Aug. 22, 2023

(65) Prior Publication Data

US 2024/0070585 A1 Feb. 29, 2024

Related U.S. Application Data

(60) Provisional application No. 63/400,125, filed on Aug. 23, 2022.

(51) Int. Cl.
*G06Q 10/0635* (2023.01)
*G06N 20/00* (2019.01)
*G06Q 10/0639* (2023.01)
*G16H 40/20* (2018.01)

(52) U.S. Cl.
CPC ......... *G06Q 10/0635* (2013.01); *G06N 20/00* (2019.01); *G06Q 10/06393* (2013.01); *G16H 40/20* (2018.01)

(58) Field of Classification Search
CPC ......... G06Q 10/0635; G06Q 10/06393; G06N 20/00; G06N 3/045; G06N 3/0475; G16H 40/20; G16H 10/60; G16H 50/30
See application file for complete search history.

(56) References Cited

U.S. PATENT DOCUMENTS

| | | |
|---|---|---|
| 2014/0358585 A1 | 12/2014 | Reiner |
| 2018/0308569 A1 | 10/2018 | Luellen |
| 2018/0357886 A1 | 12/2018 | Tavori et al. |
| 2019/0279767 A1 | 9/2019 | Bates |
| 2020/0090089 A1 | 3/2020 | Aston et al. |
| 2021/0103991 A1 | 4/2021 | Kern et al. |
| 2021/0398657 A1 | 12/2021 | Johnson et al. |
| 2024/0233895 A1* | 7/2024 | LaBorde .............. G05D 1/0088 |

FOREIGN PATENT DOCUMENTS

CN 110403773 A * 11/2019

OTHER PUBLICATIONS

Abe, A; Kogure, K; Hagita, N. "Nursing risk prediction as chance discovery." Springer-Verlag Berlin, 2004.) (Year: 2004).*

* cited by examiner

*Primary Examiner* — Linh Giang Le
(74) *Attorney, Agent, or Firm* — Finch & Maloney PLLC

(57) ABSTRACT

In an illustrative embodiment, systems and methods are provided for combining disparate data sets gathered from a variety of external resources to produce safety metrics related to healthcare facilities, correlating data elements derived from the data sets to identify variables that impact safety incident risk in a medical facility environment, and normalizing patient outcomes with underlying population wellness data to allow for benchmarking across facilities and/or geographic regions.

12 Claims, 15 Drawing Sheets

FIG. 4D

MEDICAL LIABILITY PREVENTION, MITIGATION, AND RISK QUANTIFICATION

RELATED APPLICATIONS

This application claims priority to U.S. Provisional Patent Application Ser. No. 63/400,125, entitled "Medical Liability Prevention, Mitigation, and Risk Quantification" and filed Aug. 23, 2022. All above identified applications are hereby incorporated by reference in their entireties.

BACKGROUND

Today's healthcare industry must manage risks including malpractice claims, workers' compensation costs, and other liabilities in a very competitive environment with reduced reimbursement. Frequent causes of medical malpractice claims include misdiagnosis, delayed diagnosis, infection, medication errors, and surgical errors. However, the circumstances that give rise to greater risk of these errors and other safety issues can be difficult for a healthcare facility to pinpoint and mitigate prior to the malpractice claims being filed. Additionally, due to differences in patient demographics and underlying population health from geographic location to geographic location, healthcare providing systems can find it hard to judge whether an individual facility's industry safety ratings are indicative of efforts at the facility itself or just a side effect of the patient population obtaining services at the facility.

The inventors identified a need for healthcare facility performance assessment that can provide actionable insights for improved performance, quality, patient safety and reduced costs.

SUMMARY OF ILLUSTRATIVE EMBODIMENTS

The present disclosure describes healthcare industry solutions designed to leverage healthcare facility data and other external data to generate analytics-based assessments of healthcare facilities' overall performance—using industry metrics, key performance indicators (KPIs), and innovative benchmarks—to provide actionable insights for improved performance, quality, patient safety, and reduced costs.

In one aspect, the present disclosure relates to systems and methods for combining disparate data sets gathered from a variety of external resources to produce safety metrics related to healthcare facilities. The data sets, for example, may include industry safety ratings, patient ratings of healthcare facilities, medical malpractice litigation documents, medical malpractice claims records, worker compensation claims, accident reports, claimant demographics, patient demographics, and/or facility financial data.

In one aspect, the present disclosure relates to systems and methods for correlating data elements to identify variables that impact safety incident risk in a medical facility environment. The identified variables, for example, may be analyzed to find solutions that mitigate the risk of malpractice claims. In some embodiments, data elements may be correlated through applying machine learning algorithms to medical malpractice claims data, accident report data, and/or workers' compensation claims data for one or more healthcare facilities.

In one aspect, the present disclosure relates to systems and methods for normalizing patient outcomes with underlying population wellness data to allow for benchmarking across facilities and/or geographic regions. Community risk factors and/or health outcome factors for a patient population or the geographic location of a given facility may be applied to normalize sets of data in view of underlying health risk factors.

The foregoing general description of the illustrative implementations and the following detailed description thereof are merely exemplary aspects of the teachings of this disclosure and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIGS. 4B through 4E illustrate screen shots of example user interfaces presenting various metrics that may be generated using the example process of FIG. 4A;

DETAILED DESCRIPTION OF ILLUSTRATIVE EMBODIMENTS

Figure 1:
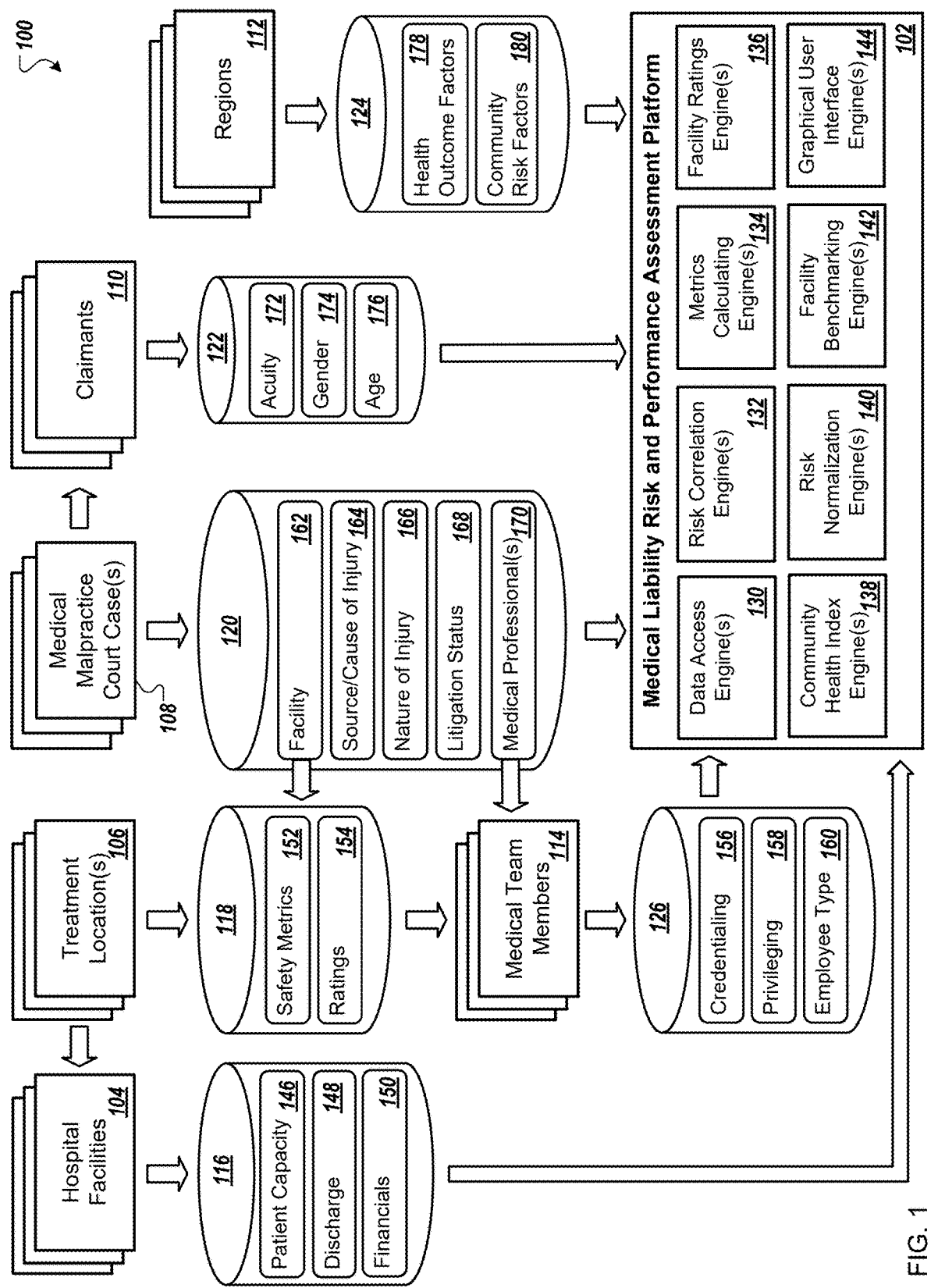
FIG. 1 is a block diagram of an example system and environment for performing medical liability risk and performance assessments.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

FIG. 1 is a block diagram of an example platform 102 and environment 100 for performing medical liability risk and performance assessments. The medical liability risk and performance assessment platform 102 obtains data from multiple external sources, organizes the data, and combines the data to generate a deeper assessment of ratings and assessments of various hospital facilities 104 and/or other medical treatment locations 106. In some embodiments, in addition to reviewing ratings and assessments associated with a topic medical facility, the platform 102 additionally obtains information regarding the facility's patient base, the extended community makeup, and/or other aspects of the facility to normalize ratings and safety measures, thereby supporting normalized comparison metrics.

In some implementations, the platform 102 includes one or more data access engines 130 for obtaining data from third party systems, such as hospital facility data 116 regarding a set of hospital facilities 104, treatment location data 118 regarding a set of treatment locations 106, and medical team members 114 of the treatment locations 106 and/or hospital facilities 104. The data may also include malpractice litigation data 120 related to a set of medical malpractice court cases 108 filed against one or more of the hospital facilities 104 and/or the treatment locations 106 as well as claimant data 122 regarding claimants 110 associated with the medical malpractice court cases 108. Further, the data may include regional health metric data 124 encompassing a set of regions 112 or communities in which the various treatment locations 106 and/or hospital facilities 104 are located.

The data access engines 130, in some implementations, collect facility data 116 from the systems of the various treatment locations 106/hospital facilities 104 and/or from a regional or national data source, such as the American Hospital Directory by American Hospital Directory, Inc. of Louisville KY. The facility data 116, in some examples, may include patient capacity data 146 (e.g., number of beds, number of intensive care beds, etc.), patient discharge data 148 (e.g., total annual discharges, total patient days spent at the hospital, average days to discharge, median days to discharge, average/median days to discharge per service category, etc.), financial data 150 (e.g., total patient revenue, average charges per patient, average charge per patient per service category, non-patient revenue, net income, etc.), and/or outpatient data (e.g., number of patients per outpatient service category).

In some implementations, the data access engines 130 collect treatment location data 118 regarding one or more treatment locations 106 and/or hospital facilities 104 from one or more safety and ratings services such as, in some examples, the Centers for Medicare & Medicaid Services (CMS) Star Rating Assessments by the U.S. government, U.S. News Hospital Ratings by U.S. News & World Report L.P. of New York, NY, and/or Healthgrades assessments by Healthgrades Marketplace, LLC of Denver, CO. The treatment location data 118, for example, may include safety metrics 152 and/or patient ratings 154. In addition to safety metrics 152, in some embodiments, the treatment location data 118 includes internally collected safety data, such as incident reports related to accidents within the location 106 or hospital facility 104. The internal safety data, for example, may include a variety of safety events, accidents, mistakes, and/or causes of injury, along with pertinent details such as time of day, day of week, type of bed, place of occurrence of each event, department or service unit, and/or medical team members 114 involved.

The data access engines 130, in some implementations, collects medical team member data 126 regarding medical team members 114 of the treatment locations 106 and/or hospital facilities 104. The data, for example, may be provided by the treatment locations 106 and/or hospital facilities 104. The medical team member data 126, in some examples, may include credentialing data 156, privileging data 158 (e.g., for medical team members 114 working within certain treatment locations 106 and/or hospital facilities 104 without being an employee of the treatment location 106 or hospital facility 104), and/or employee type 160. Further medical team member data 126 may include, in some examples, departments, service units, schedules, and/or length of employment.

In some implementations, the data access engines 130 collect litigation data 120 regarding medical malpractice cases 108. The litigation data, for example, may identify a facility 162 (e.g., hospital facility 104 and/or treatment location 106) as well as one or more medical team members 114 (e.g., medical professionals 170) associated with the malpractice accusation. The data access engines 130, for example, may link the medical malpractice data 120 with the treatment location data 118, hospital facilities data 116, and/or medical team member data 126 for data analytics purposes. The litigation data 120, as illustrated, may also include a source and/or cause of injury 164 to the patient, a nature of the injury 166, and/or a status of the litigation 168. In some embodiments, the data access engines 130 additionally collect data regarding each claimant 110 named in the medical malpractice cases 108 as claimant data 122. The claimant data 122, for example, may include one or more acuities 172 of the claimant, a claimant's gender 174 of the claimant, and/or a claimant's age 176. The one or more acuities, in some examples, can include allergies, co-morbidities, disorders, and/or diseases that could cause the claimant 110 to be more susceptible to or at higher risk for the associated injury 166. The acuities 172, in further examples, can include acuities that may contribute to a breakdown in communication with staff such as, in some examples, foreign language speaker, deaf or hard of hearing, and/or mental cognition disorders/disabilities.

The data access engines 130, in some implementations, collects regional data 124 regarding geographic regions of the treatment locations 106 and/or hospital facilities 104 to assess general community health. In collecting health outcome factors 178 and/or community risk factors 180, for example, the platform 102 may normalize data from region to region, taking into account health disparities (e.g., population age distribution, commonality of lifestyle factors such as obesity rates, smoking rates, and/or alcohol consumption rates, commonality of co-morbidities such as diabetes, heart disease, and/or high blood pressure, major industries employing workers to positions involving significant inherent risks, etc.) such that comparisons may be made among disparate geographic regions.

The data access engines 130, in some implementations, categorize data using a set of standard labels for metrics generation, comparison, combination, and correlation purposes. For example, individual treatment locations 106 and/or hospital facilities 104 may use different codes or titles for various types of data. Further, medical facilities generally have migrated to logging more and more detailed and precise information. However, the level of precision in the information causes difficulties for data analysis since trends cannot be derived when very similar events and/or injuries are logged with a granular level of specificity.

Figure 2A:
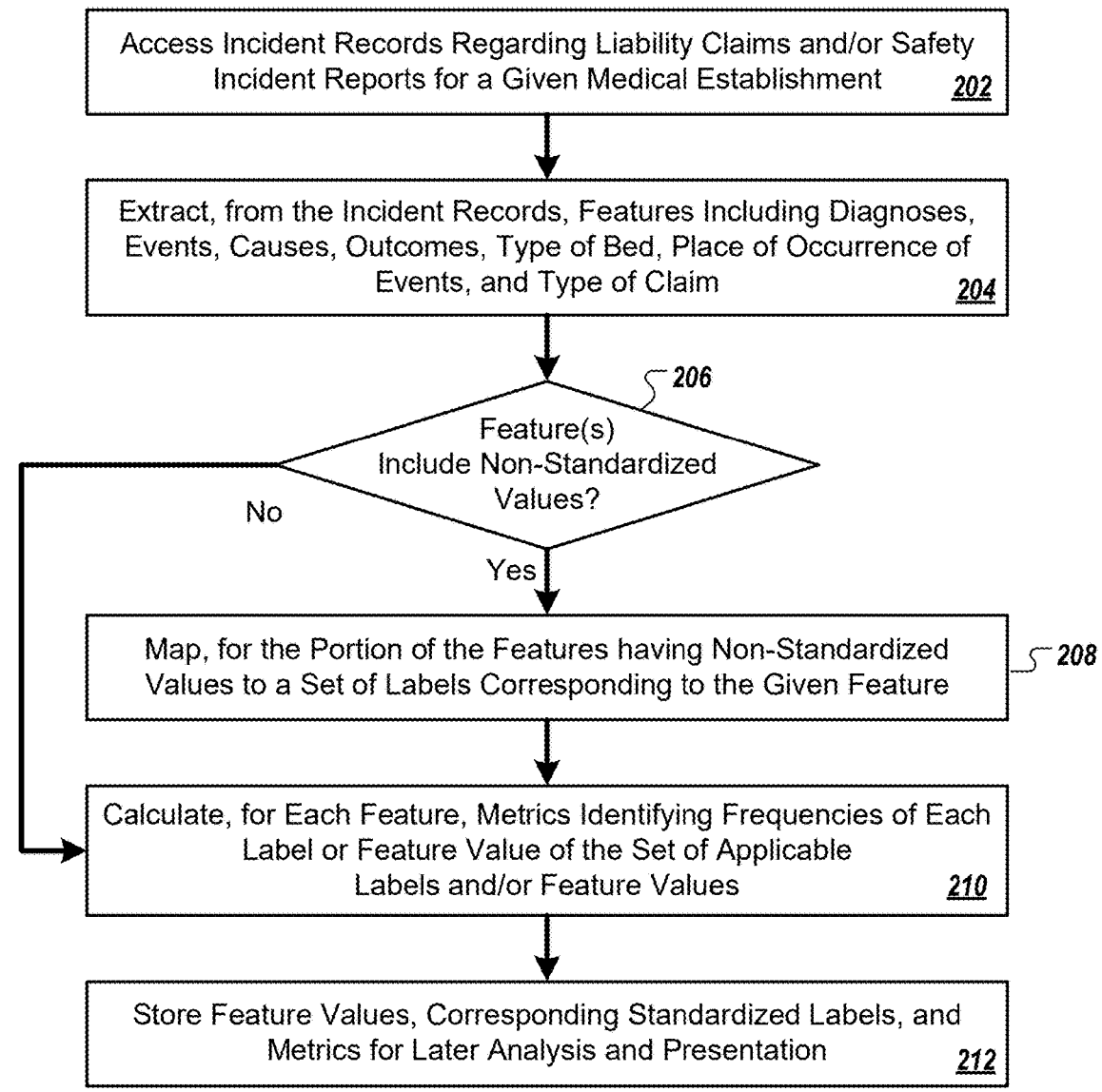
FIG. 2A is a flow chart of an example method for mapping incident report features to a set of standardized labels.

Turning to FIG. 2A, a flow chart illustrates an example method 200 for grouping synonymous or closely related terms in a set of records by applying a set of standardized labels to certain data terms in the records. The method 200, for example, may be used for grouping recorded data elements into categories defined by actionable terms such that metrics and comparisons may be achieved. The original terms in the records data, in some examples, may include medical malpractice profiles referencing various similar or related terms, injury types, diagnoses, descriptions, and/or outcomes. The method 200, in some embodiments, is performed by the medical liability risk and performance assessment platform 102 of FIG. 1.

In some implementations, the method 200 begins with accessing incident records regarding liability claims and/or safety incident reports for a given medical establishment (202). The records, for example, may be collected by the data access engines 130 from the treatment locations 106, hospital facilities 104, and/or medical malpractice court cases 108.

In some implementations, data features are extracted from the incident records (204). The data features, for example, may include diagnoses, events, causes, outcomes, type of bed, place of occurrence of an event, and/or a type of claim. At least a portion of the features, for example, may be extracted from formatted data records exported from the medical facility system. In another example, a portion of the features may be extracted from an insurance claim form, such as a malpractice claim.

In some implementations, if a portion of the features include non-standardized values (206), the portion of the features having non-standardized values are mapped to a set of standardized labels (208). The standardized labels, for example, group similar and/or synonymous terms into a smaller set of actionable terms for data analytics purposes. In standardizing terms, in another example, differing medical organizations having differing data organization structures may be compared, regardless of any data term reduction (e.g., grouping) that may be achieved. The labels, for example, may replace the corresponding feature and/or be added to the data record having the feature (e.g., as a standardized label field of each record).

In some implementations, for each feature of a portion of the extracted features, metrics identifying frequencies of each label or feature value of the set of applicable labels and/or feature values are calculated (210). The frequency metrics, for example, may be used to identify the most frequent circumstances occurring in the set of accidents, mistakes, malpractice insurance claims, etc. represented by the incident records. In some examples, frequencies may be calculated regarding diagnoses, work shifts, types of bed, types of events, causes of the accidents or injuries, locations of the accidents or injuries, and/or outcome of the accidents/injuries. The metrics, for example, may be calculated by one or more metrics calculating engines 134 of the platform 102 of FIG. 1.

In some implementations, the feature values, corresponding standardized labels, and frequency metrics are stored for later analysis and/or presentation (212). The data, for example, may be stored by the medical liability risk and performance assessment platform 102 of FIG. 1. The data may be formatted in a database, data warehouse, or other linked data storage architecture for query access.

Figure 2B:
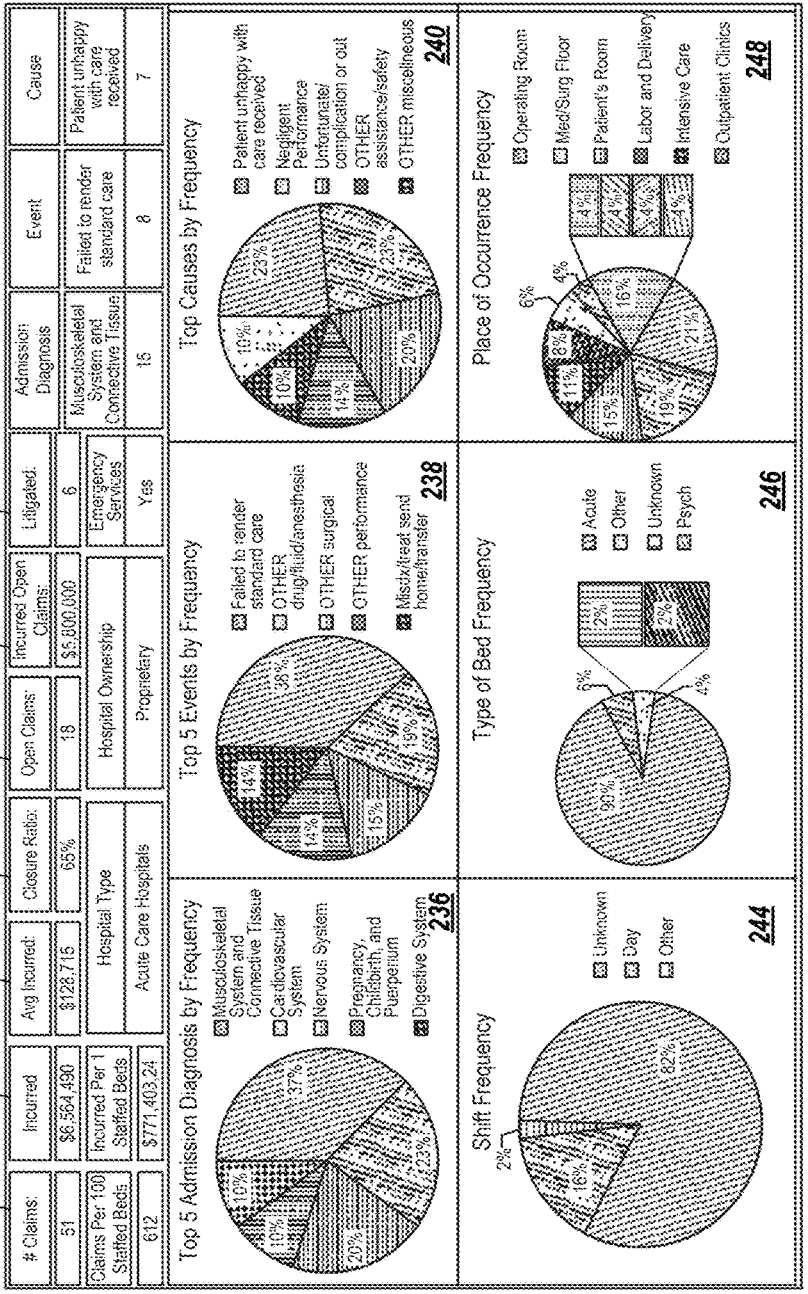
FIG. 2B and FIG. 2C illustrate portions of a screen shot of an example user interface for reviewing metrics related to incident reports.

Turning to FIG. 2B, a screen shot of an example incident metrics user interface 220 presents comparison analysis of frequency metrics for various components of a set of malpractice insurance claims 222 (e.g., 51 claims). At a top of the user interface 220, a left-hand section presents data related to the claims 222, including costs incurred 224 ($6,564,490), average cost incurred 226 ($128,715), closure ratio 228 (65%), a number of open claims 230 (18), costs incurred for the presently open claims 232 ($5,800,000), and a number of claims litigated 234 (6).

The user interface 220 additionally presents a set of pie charts, one for each data feature, such as the features described in relation to FIG. 2A. The features, for example, include admission diagnosis, event, cause, final outcome, shift, type of bed, place of occurrence, and type of claim.

A first pie chart 236 illustrates top admission diagnosis by frequency, broken down by percentages of musculoskeletal system & connective tissue, cardiovascular system, digestive system, nervous system, pregnancy, childbirth, & postpartum, and unknown.

A second pie chart 238 illustrates top events by frequency, including failure to render standard care, other drugs/fluid/anesthesia, other surgical, other performance, and misdiagnosis/treatment leading to sending home/transferring.

Top causes by frequency are presented in a third pie chart 240, including patient unhappy with care received, negligent performance, unfortunate/complication or out, other assistance/safety, and other miscellaneous.

In a fourth pie chart 242, top final outcomes by frequency are illustrated, including outcomes of death, additional admissions/treatment/surgery, unplanned surgery, pain & suffering, and broken teeth.

A fifth pie chart 244 details shift frequency, including unknown, day, evening, and other.

In a sixth pie chart 246, type of bed frequency may include acute, other, unknown, bassinette, psych, and long-term care.

A seventh pie chart 248 illustrates place of occurrence frequency, including operating room, medical/surgical floor, labor & delivery, the patient's room, intensive care, and outpatient clinics.

Finally, types of claim frequency is illustrated in a last pie chart 250. The types include commercial general liability (CGL), hospital professional liability (HPL), and products and public liability (PPL).

In an upper right-hand area, the most common label of each feature is listed, for the features represented in the pie charts 236 through 248.

Figure 2C:
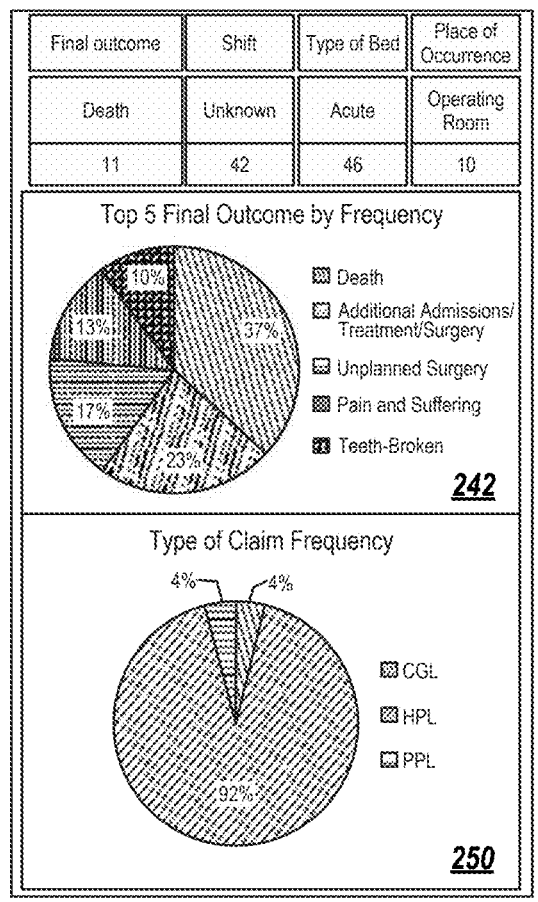

Returning to FIG. 1, in some implementations, the platform 102 includes one or more risk correlation engines 132 for identifying potential causation for increased malpractice liabilities in a particular hospital facility 104 or treatment location 106. The risk correlation engines 132, for example, may conduct machine learning on the features extracted by the data access engines 130 and/or mapped to standardized labels through the method 200 of FIG. 2A. The risk correlation engines 132, for example, may analyze combinations of the features presented in the metrics of the portions of a screen shot 220 of FIG. 2B and FIG. 2C (e.g., diagnosis, event, cause, outcome, shift, type of bed, place of occurrence, and/or type of claim). Further, the risk correlation engines 132 may map claim data to further details, such as medical team members (e.g., employee type 160, privileging 158, and/or credentialing 156), claimants (e.g., acuity 172, gender 174, and/or age 176).

Figure 3A:
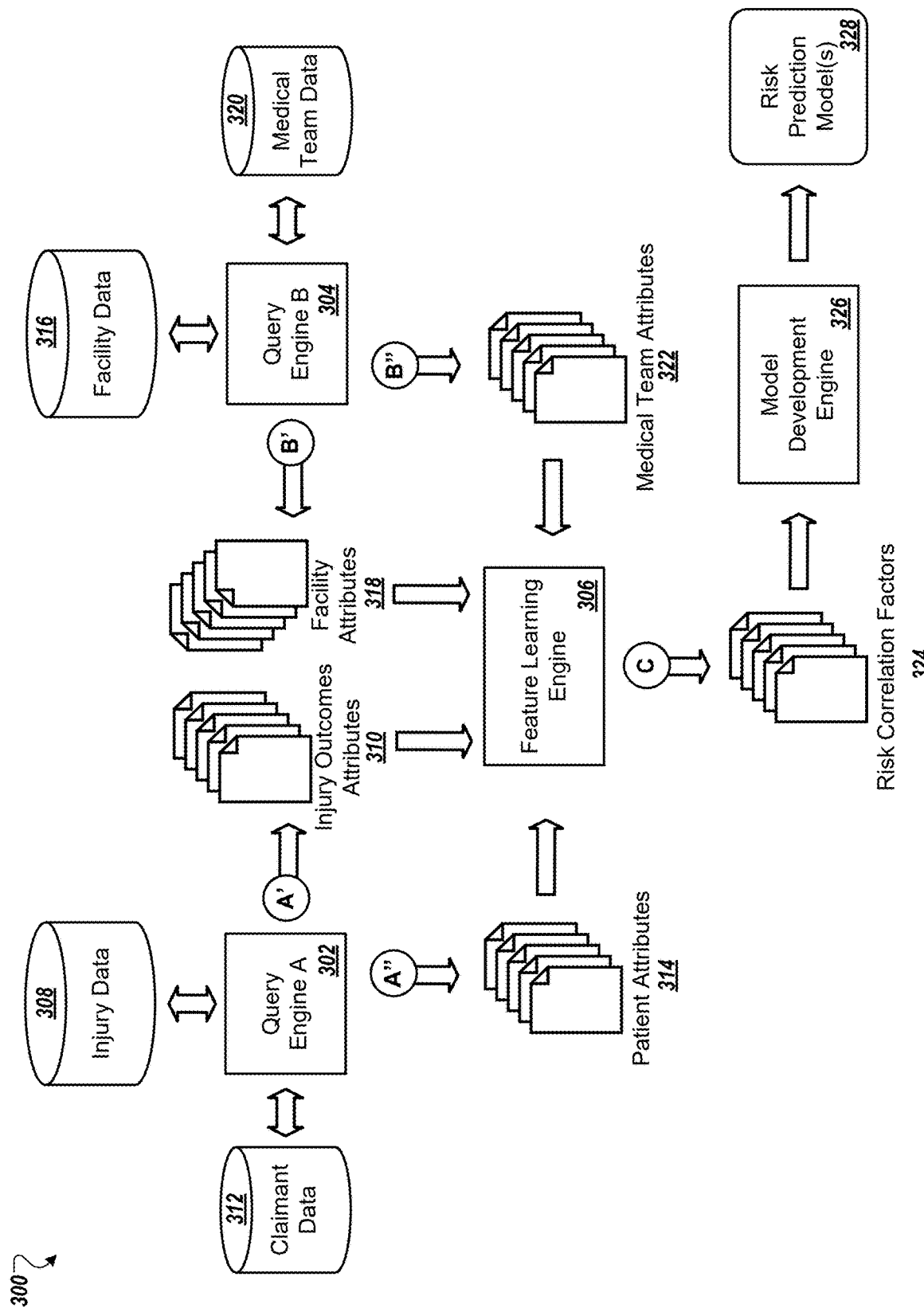
FIG. 3A is an operational flow diagram of an example process for deriving risk correlation factors related to medical incidents.

Turning to FIG. 3A, an operational flow diagram presents an example process 300 for applying machine learning analysis to medical incident data records to identify factors indicative of an increased likelihood of adverse outcome. Factors identified by the process 300 may be included in one or more models for predicting adverse outcome likelihoods based on current facility information (e.g., hospital facility data 116, medical team member data 126, etc. of FIG. 1). The models, for example, may include one or more machine learning classifiers, neural networks, and/or artificial intelligence models.

In some implementations, the process 300 begins with obtaining, by a first query engine 302 from injury data 308, injury outcomes attributes 310 identifying attributes related medical injuries. The injury data 308, for example, may include the source/cause of injury data 164 and/or the nature of injury data 166 related to the medical malpractice court cases 108 of FIG. 1. The injury outcomes attributes 310 may represent medical incidents over a period of time, such as three months, six months, one year, or multiple years. Each injury outcome represented by the injury outcomes attributes 310 is associated with a particular patient (e.g., claimant) within a patient population.

The injury outcomes attributes 310, in some examples, may each include attributes of one or more medical professionals involved in the injury, one or more departments of the facility involved in the injury, one or more regions of the facility involved in the injury, one or more services provided by the facility leading to the injury, a time of day of injury, a date of injury, a source of injury, a cause of injury, a nature of injury, a type of bed, and/or a final outcome caused by the injury. Certain injury outcomes attributes 310, for example, may include factors illustrated in the portions of the screen shot 220 of FIG. 2B and FIG. 2C. Further, aspects of the attributes may be mapped to features of the facility, such as the time of day being mapped to a work shift within a hospital facility.

In some implementations, the first query engine 302 obtains, from claimant data 312, patient attributes 314 regarding a patient population. The patient attributes 314 may include, in some examples, attributes of acuity 172, gender 174, and/or age 176, as discussed in relation to claimant data 122 of FIG. 1.

In some implementations, the second query engine 304 obtains, from facility data 316, facility attributes 318 regarding a subject medical facility. In some examples, the facility attributes 318 may include patient capacity data 146, discharge data 148, safety metrics 152, and/or ratings 154 as described in relation to FIG. 1. Further, the facility attributes 318 may include medical equipment availability, services provided, specialties offered, accreditations, and/or affiliations (e.g., hospital affiliations, academic affiliations). The facility attributes 318 may differ based on type of facility, services offered by the facility, and/or region of the facility.

The second query engine 304, in some implementations, obtains, from medical team data 320, medical team attributes 322 regarding medical professionals involved in the medical injury incidents. The medical team attributes 322, in some examples, may include features such as credentialing, privileging, employee type, and/or experience level (e.g., years or experience, seniority level, etc.). Further, the medical team attributes 322 may include, in some examples, indicators of facility-provided staff training (hours, levels, accreditation) in patient care, safety topics, or other procedures.

In some implementations, a feature learning engine 306 obtains the medical team attributes 322, the patient attributes 314, the injury outcomes attributes 310, and the facility attributes 318 and analyzes the information to determine a set of risk correlation factors 324 identifying attributes and values or value ranges correlated with increased risk of patient injury. The feature learning engine 306, for example, may include one or more regression models, artificial intelligence models, and/or neural networks for identifying strongly correlating risk factors within the data set. Certain risk correlation factors 324, in turn, may correspond to a particular facility attribute 318, medical team attribute 322, and/or patient attribute 314. Further, some risk correlation factors 324 may be identified as sets of attributes (e.g., safety metric A within a range of X, medical team member attribute B, and service C corresponds to a heightened likelihood of patient injury).

The risk correlation factors 324 may be further refined to identify those factors controllable by the medical facility. For example, patient factors, such as acuity, gender, and age, are not factors that can be manipulated by the facility—patients come as they are. However, medical team credentialing and training, staffing per shift, and department capacities are all under the control of the medical facility. Further, a facility may opt to adjust malpractice insurance coverage understanding that a particular service or specialty includes inherent risks leading to a higher likelihood of patient injury.

Figure 3B:
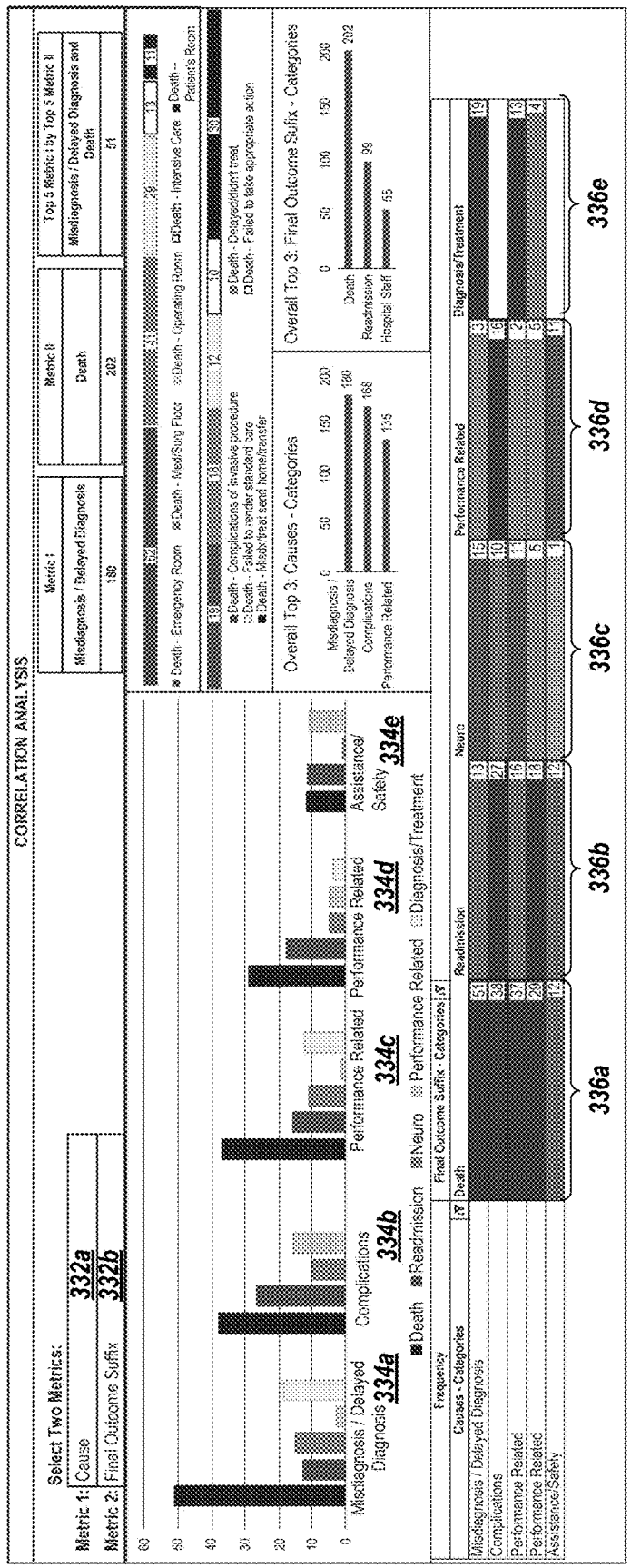
FIG. 3B illustrates a correlation analysis user interface presenting correlations between a selected pair of metrics.

In some implementations, factors may be presented in a user interface for review by an end user. The factors, for example, may be applied as metrics in comparing data related to outcomes. An example user interface 330, presented in FIG. 3B, illustrates a manual application of deriving correlations based on selection of two metrics. A similar interface may be presented in relation to automatically derived factors to review metrics related to the correlated factors.

The risk correlation factors 324, in some implementations, are used to populate additional models for predicting risk. For example, the risk correlation factors 324 may be obtained by a model development engine 326 to develop one or more risk prediction models 328 using, for each model, a portion of the risk correlation factors 324. The model development engine 326, for example, may obtain training data from historic records (e.g., facility data 116, location data 106, claimant data 110, malpractice claim data 120, and/or medical team member data 126 of FIG. 1) to train the risk prediction models 328 (and/or to tune foundational models) for use in identifying potential risk sources based on data related to a given medical facility.

In some implementations, the risk correlation engine(s) 132 of FIG. 1 generate correlation metrics based on user inputs to a graphical user interface, such as the example user interface 330 of FIG. 3B. Turning to FIG. 3B, the example user interface 330 provides a set of correlation analysis metrics and comparisons based on user selection of input metrics 332. As illustrated, the selections include a cause metric 332a and a final outcome metric 332b. Metrics are arrange illustrating both causes 334 (misdiagnosis/delayed diagnosis, complications, performance-related, and assistance/safety) and final outcomes 336 (death, readmission, neuro, performance-related, and diagnosis/treatment). The correlation data may be derived from a past year, a past three years, or a past five years. As illustrated, the metrics include frequencies, color-coded from fewest (light blue) to greatest (dark red).

The correlation analysis, in some embodiments, includes benchmarking each correlation to peer facilities, all regional facilities, and/or all national facilities. For example, in other implementations, benchmark indicators may be presented on each of the bar graphs representing benchmark counts for each type of cause 334a-e.

Returning to FIG. 1, in some implementations, one or more facility ratings engines 136 develops metrics for comparison ratings of the treatment locations 106 and/or hospital facilities 104. The ratings engine(s) 136, for example, may combine safety metrics 152 and/or ratings 154 collected by the data access engine(s) 130 from various public and/or third-party sources for developing customized metrics related to safety, quality of care, and/or patient feedback. Examples of various facility ratings metrics are presented in screen shots of FIG. 4B through FIG. 4E, described below.

Figure 4A:
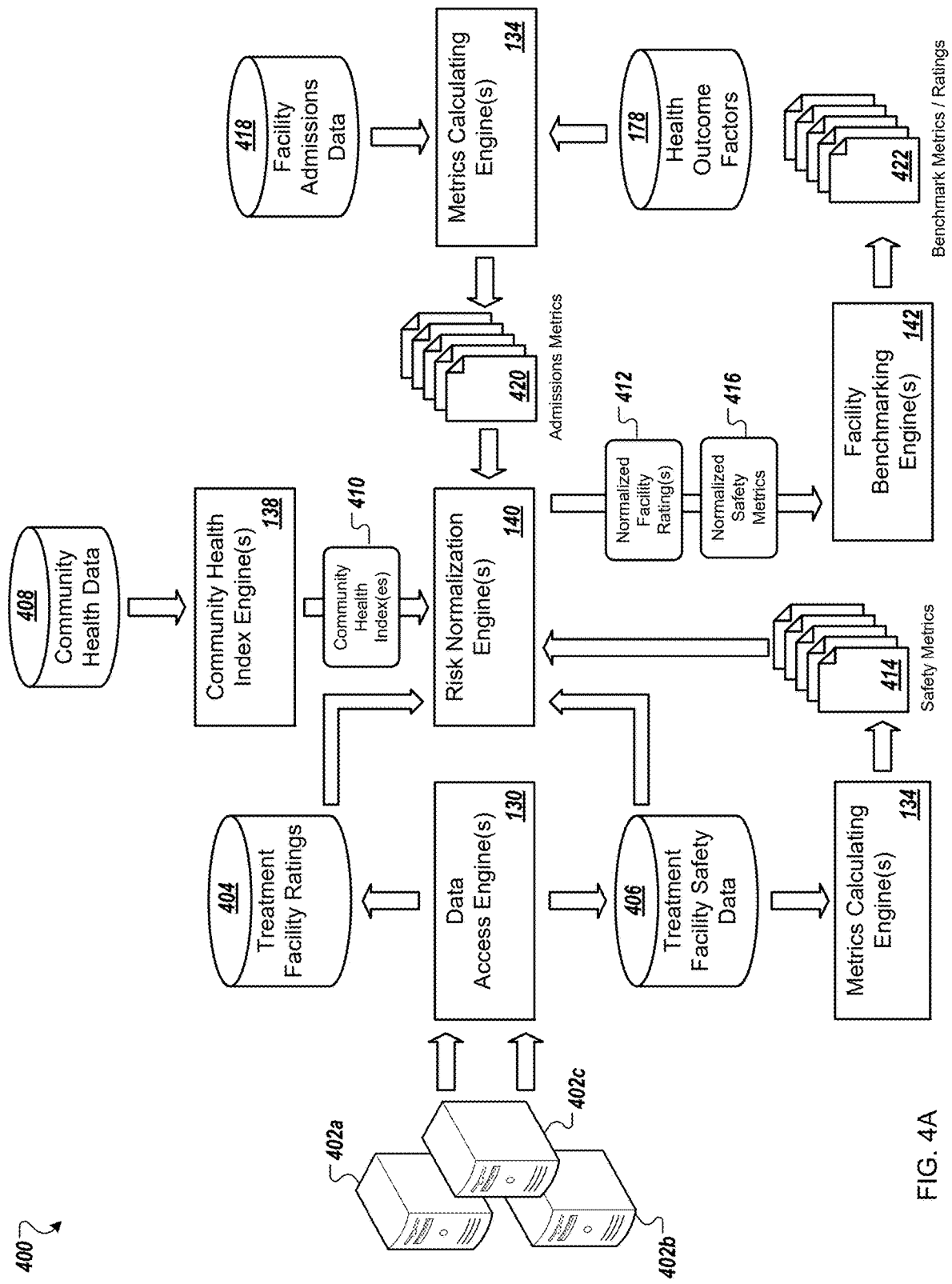
FIG. 4A illustrates an operational flow diagram of an example process for calculating facility ratings and benchmark metrics.

Turning to FIG. 4A, a flow diagram presents an example process 400 for generating ratings data and benchmarking metrics for treatment facilities, such as the treatment locations 106 and/or hospital facilities 104 described in relation to FIG. 1. The facility ratings engine(s) 136 of FIG. 1, for example, may coordinate at least a portion of the process 400.

In some implementations, the process 400 begins with gathering, by one or more data access engines 130, treatment facility ratings 404 (e.g., the ratings 154 of the treatment location data 118 of FIG. 1) and treatment facility safety data 406 (e.g., the safety metrics 152 of the treatment location data 118 of FIG. 1) from external data sources 402. The treatment facility ratings 404 and/or the treatment facility safety data 406, for example, may be collected on a periodic basis, such as a release basis of ratings data by each of at least a portion of the external data sources 402.

In some implementations, the metrics calculating engine(s) 134 each calculate safety metrics 416 from the treatment safety data 406. The safety metrics 416, in some examples, may include rates of complications, rates of infection, and/or rates of other adverse outcomes. FIG. 4C, for example, infection rate safety metrics include catheter-associated urinary tract infections 452a, central line associated bloodstream infection 452b, Clostridium difficile (C. Diff.) infections 452c, MRSA bacteremia infections 452d, surgical site infection (SSI) rate for abdominal hysterectomy 452e, and SSI rate for colon surgery 452f. In another example, turning to FIG. 4D, medical complications may include post-operative complications 462a (e.g., a wound splitting open after surgery, post-surgical blood stream infection, broken hip from a post-surgical fall, serious post-surgical blood clots, postoperative acute kidney injury requiring dialysis, postoperative respiratory failure, etc.), perioperative complications 462b (e.g., hemorrhage or hematoma, etc.), and/or medical treatment complications 462c (e.g., accidental cuts and tears, collapsed lung, etc.). Further, rates of death per disease category 470, such as, in some examples, heart attack patients, heart failure patients, pneumonia patients, chronic obstructive pulmonary disease (COPD) patients, coronary artery bypass graft (CABG) patients, and/or stroke patients, as illustrated in FIG. 4D, may be calculated. The safety metrics 416, further, may include hospital readmissions, emergency room visits, and/or other unplanned hospital visits per discharged patient. Turning to FIG. 4E, for example, readmission rate metrics may be calculated per disease category 470 and/or per outpatient procedure category 482. Further, readmission metrics may be calculated based on a rate of readmission post discharge and/or a number of hospital return days per 100 discharges. Other examples of safety metrics include frequency of patient falls and injuries, frequency of dangerous bed sores, and frequency of miscommunication about medicines.

In some implementations, the treatment facility ratings 404 and/or the safety metrics 414 are normalized by one or more risk normalization engines 140 to account for varying community health in the regional demographics where the various treatment facilities are located. In some embodiments, one or more community health index engines 138 analyze community health data 408 to produce one or more community health indexes 410 which can be used as weighting factors in normalizing treatment facility ratings. The community health data 408, for example, may include the health outcome factors 178 and/or community risk factors 180 as described in relation to the regional data 124 of FIG. 1.

In some implementations, the risk normalization engine(s) 140 analyze admission metrics 420 to account for varying population factors within facility patients. For example, facility admissions data 418 may be analyzed by the metrics calculating engines 134 to generate the admissions metrics 420 related to the propensity of health outcome factors 178 among the patient population which may differ significantly from other facilities. For example, facilities with particular specialties may be magnets for patients having certain health concerns that can contribute to a variety of adverse outcomes, such that a propensity of certain health outcome factors 178 among the patient population is even greater than the community health data 408 would anticipate. In applying the admissions metrics 420 in addition to the community health index(es) 410 of in lieu of the community health index(es) 410, the risk normalization engines 140 may normalize the safety metrics 414 and/or the treatment facility ratings 404 in view of an actual standard of health of the incoming patient population.

The risk normalization engines 140, in some embodiments, apply the community health indexes 410 and/or the admissions metrics 420 to the treatment facility ratings 404 to produce normalized facility ratings 412. In some implementations, the safety metrics 414 are provided to the risk normalization engines 140 to produce normalized safety metrics 416. The normalized facility ratings 412 and/or the normalized safety metrics 416 may be provided to facility benchmarking engine(s) 142 for producing benchmarked metrics and/or ratings 422.

In some implementations, the facility benchmarking engines 142 analyze normalized facility ratings 412 and/or normalized safety metrics 416 to benchmark a set of facilities. The facilities, for example, may vary in size, specialties, geographic region, and/or patient demographics. In normalizing based upon population health (e.g., community health and/or patient population health) for each facility, the various metrics regarding the facilities may be adjusted to provide for a comparable view. The normalization allows for removing the underlying health of patient population as a contributor to ratings and/or safety factors, thereby supporting comparisons that can be used to more accurately identify facility strengths and weaknesses (e.g., factors that the facility has control over, as opposed to the health of the patients showing up at the door). The facility benchmarking engines 142 may generate benchmark metrics and/or ratings 422 for an end user review. The benchmark metrics and/or ratings 422, for example, may be used by the graphical user interface engine(s) 144 of FIG. 1 to generate reports for review by an end user.

Figure 4B:
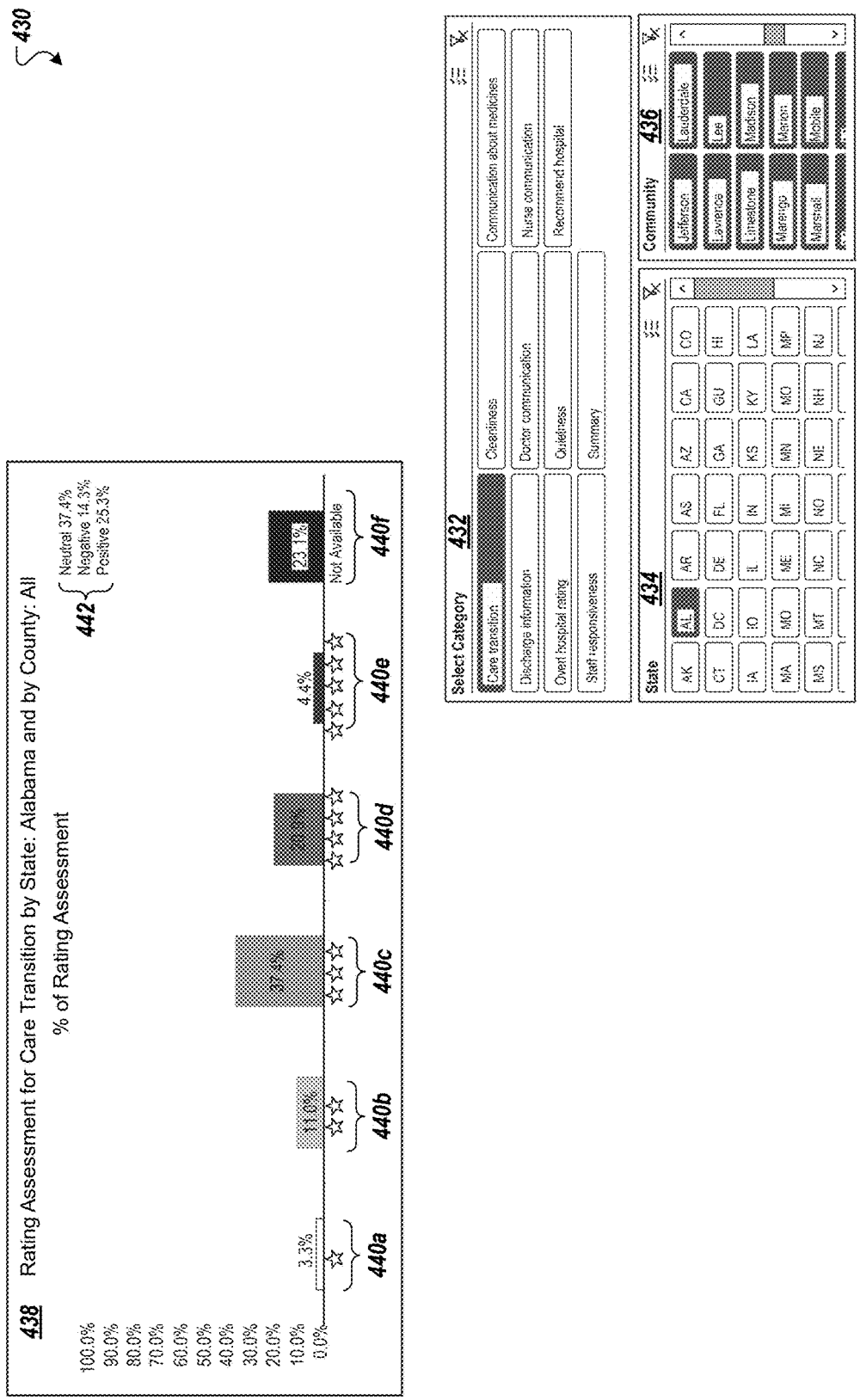
Figure 4C:
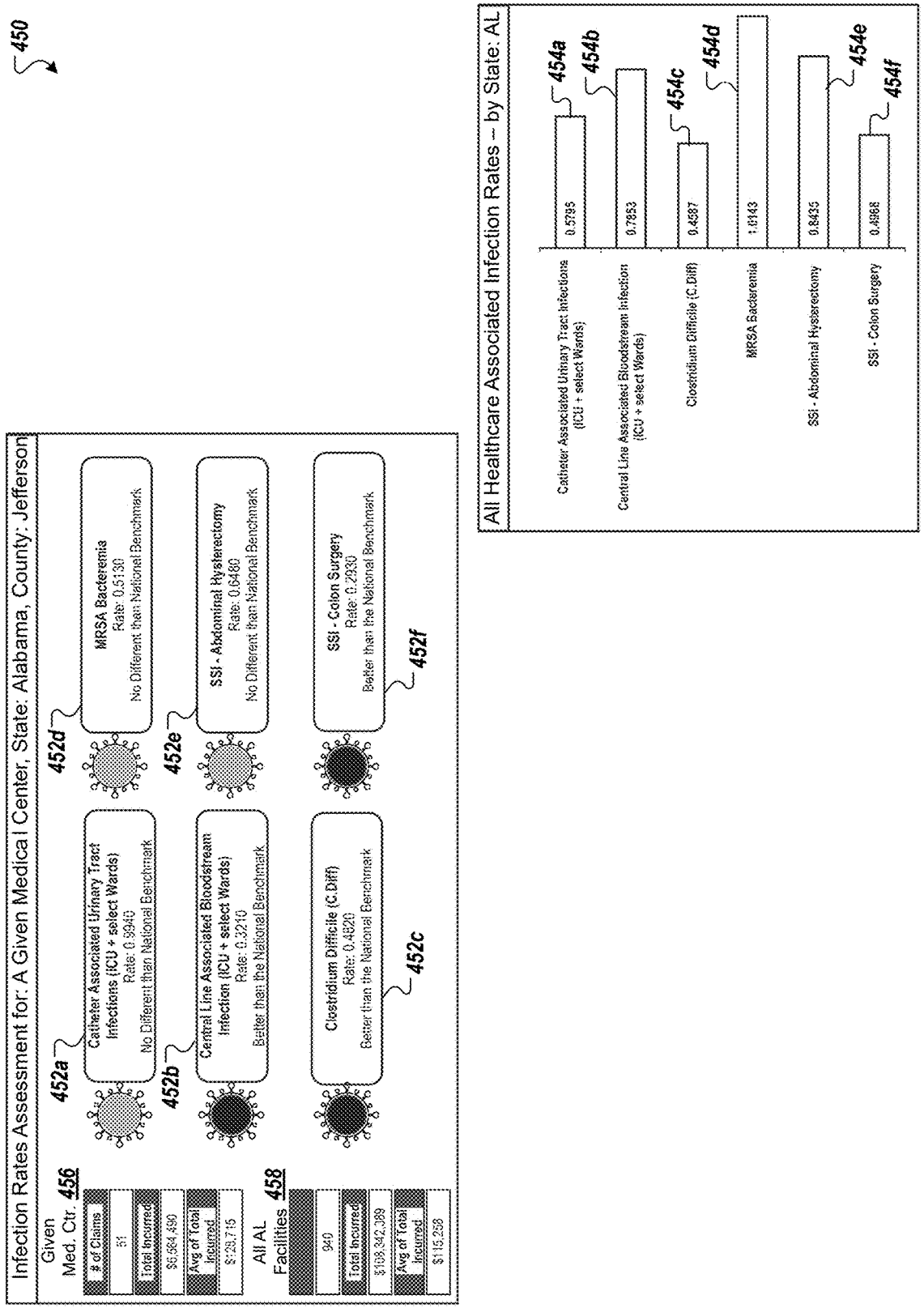
Figure 4D:
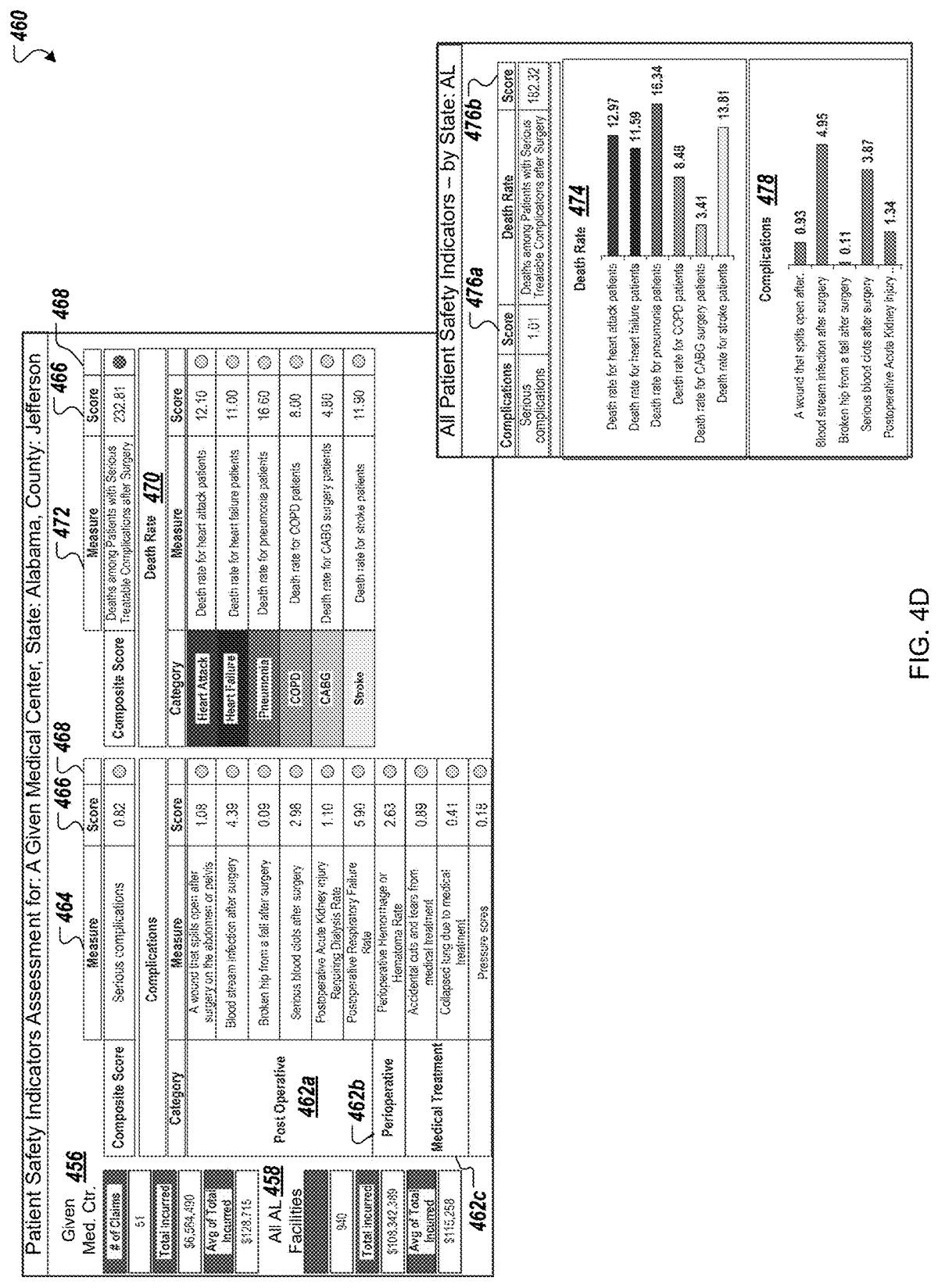
Figure 4E:
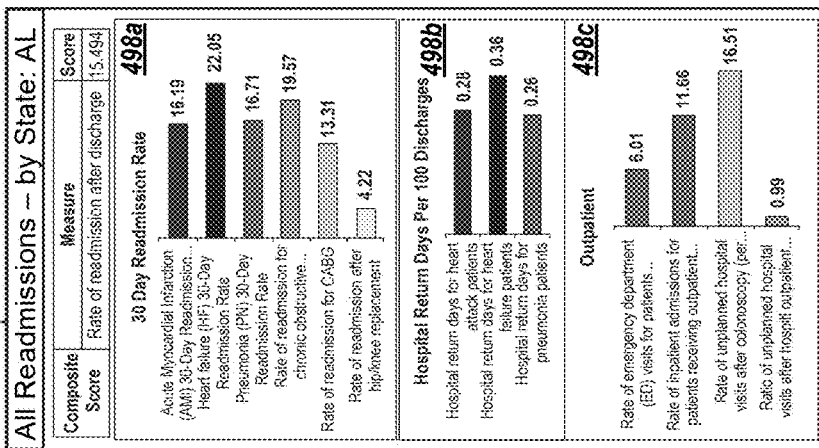

Turning to FIG. 4B, portions of a screen shot illustrate an example user interface 430 for reviewing rating assessments by category 432, state 434, and community (e.g., county, metropolitan area, city, etc.) 436. The portions of the screen shot, for example, may be illustrated side-by-side within a user display. As shown in a bar graph region 438, the rating assessments are separated into six categories 440 (e.g., one star 440a, two stars 440b, three stars 440c, four stars 440d, five stars 440e, and no rating assessment available 440f). In the bar graph region 438, ratings assessments are charted for category 432 care transition by all communities of the state of Alabama. Other categories 432 include cleanliness, communication about medicines, discharge information, doctor communication, nurse communication, overall hospital rating, quietness, recommended hospital, staff responsiveness, and summary. The categories, for example, may include categories commonly rated by one or more ratings organizations. As identified by the bar graphs, ratings information was not available 440f for nearly a quarter of the facilities in Alabama. Along with the breakdown into the six categories 440, the ratings are separated into three categories of neutral, positive, and negative 442. The facilities having unavailable ratings, in this breakdown, are identified as "neutral." In other embodiments, only rated facilities are represented in the neutral, positive, and negative categories 442 and/or in the bar graph 438.

Turning to FIG. 4C, portions of a screen shot of an example user interface 450 illustrate infection rate assessments of a given medical center in Jefferson County, Alabama in comparison to infection rates assessed across the state of Alabama. The portions of the screen shot, for example, may be illustrated side-by-side within a user display. For each type of infection 452a-452f, a corresponding rate is presented, along with an indicator regarding its comparison to a national benchmark. Further, icons presented next to each type of infection 452-452f are color-coded to the benchmark comparison (e.g., yellow corresponds to "no different than national benchmark," green to "better than the national benchmark," and red to "worse than the national benchmark"). To be indicated as "no different than the national benchmark," a rate of infection demonstrated at the given medical center may be compared to the national benchmark plus or minus a threshold difference. The threshold, in some examples, may be a set value (e.g., +=0.05, etc.), a calculated value (e.g., based on a distribution of regional benchmarks such as state-to-state comparisons), and/or a user adjustable threshold.

As illustrated in the example user interface 450, in comparison to the given medical center, infection rates by the state of Alabama 454a through 454f. In some embodiments, the comparison is made between similar facilities (e.g., hospital to hospitals, surgical center to surgical centers, etc.). In other embodiments, all facilities including data on the same metric (e.g., infection rate) are included in the analysis.

On a left side of the example screen shot 450, data metrics of number of claims (e.g., insurance claims), total expense incurred, and average of total expense incurred are presented in relation to both the given medical center 456 and all Alabama state facilities 458. In some embodiments, the data metrics relate to claims specific to infection rates. In other embodiments, the data metrics relate to all malpractice/medical injury claims regardless of reason.

Turning to FIG. 4D, for example, the same information is presented on the left side of an example screen shot 460 in relation to both the given medical center 456 and all Alabama state facilities 458. The portions of the screen shot shown in FIG. 4D as partially overlapping, for example, may be illustrated side-by-side within a user display. FIG. 4D illustrates a patient safety indicators assessment for the given medical center in Jefferson County, Alabama in comparison to patient safety indicator metrics for the entire state of Alabama. For a set of complication categories 462a-462c (e.g., post operative, perioperative, and medical treatment), various measures 464 have been allocated scores 466. A visual indicator 468 alongside each score 466 indicates whether the corresponding score is similar to (yellow), better than (green), or worse than (red) a benchmark score, such as a national score or a score for the entire state. Similar metrics are presented in relation to death rates per cause category (heart attack, heart failure, pneumonia, COPD, CABG, or stroke), with various measures 472, scores 466, and visual indicators 468.

In a section regarding the state of Alabama, a total serious complications score 476a and a total death rate score 476b is presented. Further, death rates 474 per category 470 as well as complications 478 per measure 464 are illustrated.

Turning to FIG. 4E, portions of a screen shot illustrate an example user interface 480 for presenting hospital readmissions metrics regarding a given medical center in Jefferson County, Alabama in comparison to readmissions metrics for all medical facilities in Alabama. The portions of the screen shot shown as slightly overlapping in FIG. 4E, for example, may be illustrated side-by-side within a user display. The metrics include a set of 30 day readmissions rate measures 484 and corresponding scores 486, outpatient measures 488 and corresponding scores 490, and hospital return days per 100 discharges measures 492 along with a rate of return 494. Each set of measures 484, 488, 492 includes a corresponding set of visual indicators 496 indicating whether the scores 486, 490 and/or rate of return 494 is similar than a benchmark, worse than a benchmark, or better than a benchmark comparator (e.g., national average, national median, state average, state median, etc.).

At a right side of the example user interface 480, comparative metrics are presented for all facilities in the state of Alabama, including 30 day readmission rate metrics 498a, hospital return days per 100 discharge metrics 498b, and outpatient metrics 498c.

Returning to FIG. 1, in some implementations, the community health index engines 138 analyze the community health data 124 to compare health factors across multiple communities within a region. The community granularity can include, in some examples, states, provinces, counties, metropolitan areas, or cities. The granularity applied by the community health index engine(s) 138 may be based in part on population density across the greater area (e.g., country, province, or state). At least a portion of the community health data 124, for example, may be obtained from the Center for Disease Control (CDC) and/or the environmental protection agency (EPA). The community health index engines 138 may calculate a community health index for each designated region including a set of individual sub-factors, such as disease factors, an exercise factor, an air quality factor, a water quality factor, a fresh produce accessibility factor, one or more housing quality factors, one or more educational standard factors, and/or an obesity factor. In generating a health index rating, the community health index engines 138 may apply one or more weights to certain sub-factors of the set of sub-factors.

Figure 5:
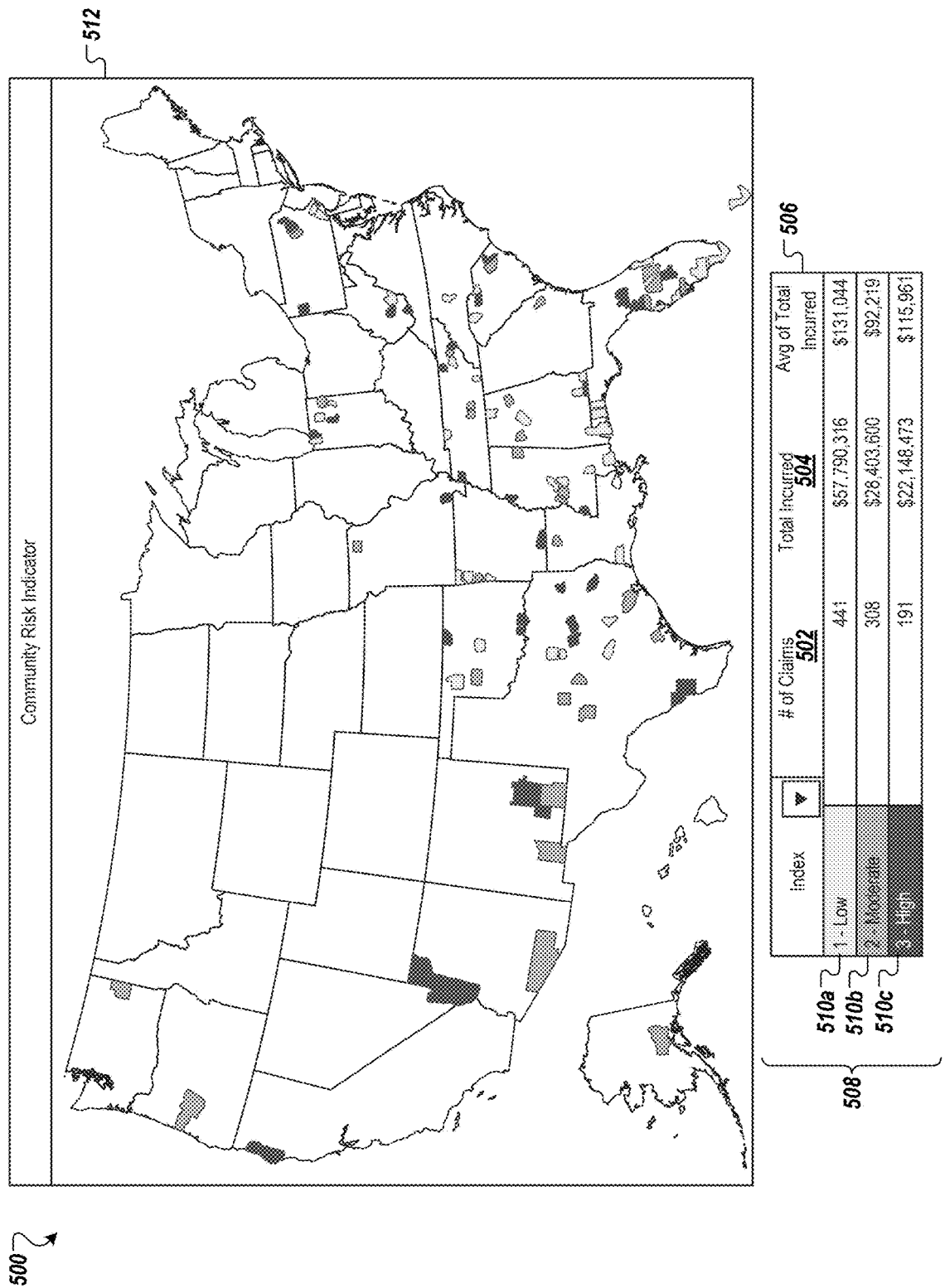
FIG. 5 illustrates an example screen shot analyzing community risk.

Turning to FIG. 5, a screen shot presents an example user interface 500 for reviewing community risk comparisons. A set of community risk levels 510, represented by color coded indications of "low" 510a, "moderate" 510b, and "high" 510c, are presented in color-codings of communities upon a map 512 as well as in a table 508 below. In the table 508, each community risk level 510 is presented in correspondence to a number of medical claims 502, a total cost incurred 504, and an average cost incurrent 506. As illustrated, the communities are distributed primarily across the west coast, south, and east of the United States. The communities, for example, may include those communities covered by a particular insurance company, those communities having a branch of a particular medical facility, or those communities having peer organizations similar to a subject medical facility.

Returning to FIG. 1, in some implementations, the medical liability risk and performance assessment platform 102 includes one or more graphical user interface engines 144 for preparing metrics displays for end-user review. As illustrated in the screen shots discussed throughout the present disclosure, the graphical user interface engines 144 may generate interactive graphical user interfaces including filters, user settings, drill-down opportunities, and/or correlation studies, allowing end users to draw intelligence from the collective data gathered by the data access engine(s) 130 and analyzed by the risk correlation engines 132, risk normalization engines 140, metrics calculating engines 134, facility ratings engines 136, and/or facility benchmarking engines 142.

Although described in relation to medical treatment facilities, in other embodiments, the architecture and engines of the platform 102 and environment 100 may be applied in assessing other industries, such as, in some examples, nursing homes, assisted living facilities, prisons, and other industries where health outcomes and safety measures may be assessed regarding a population of residents.

Figure 6A:
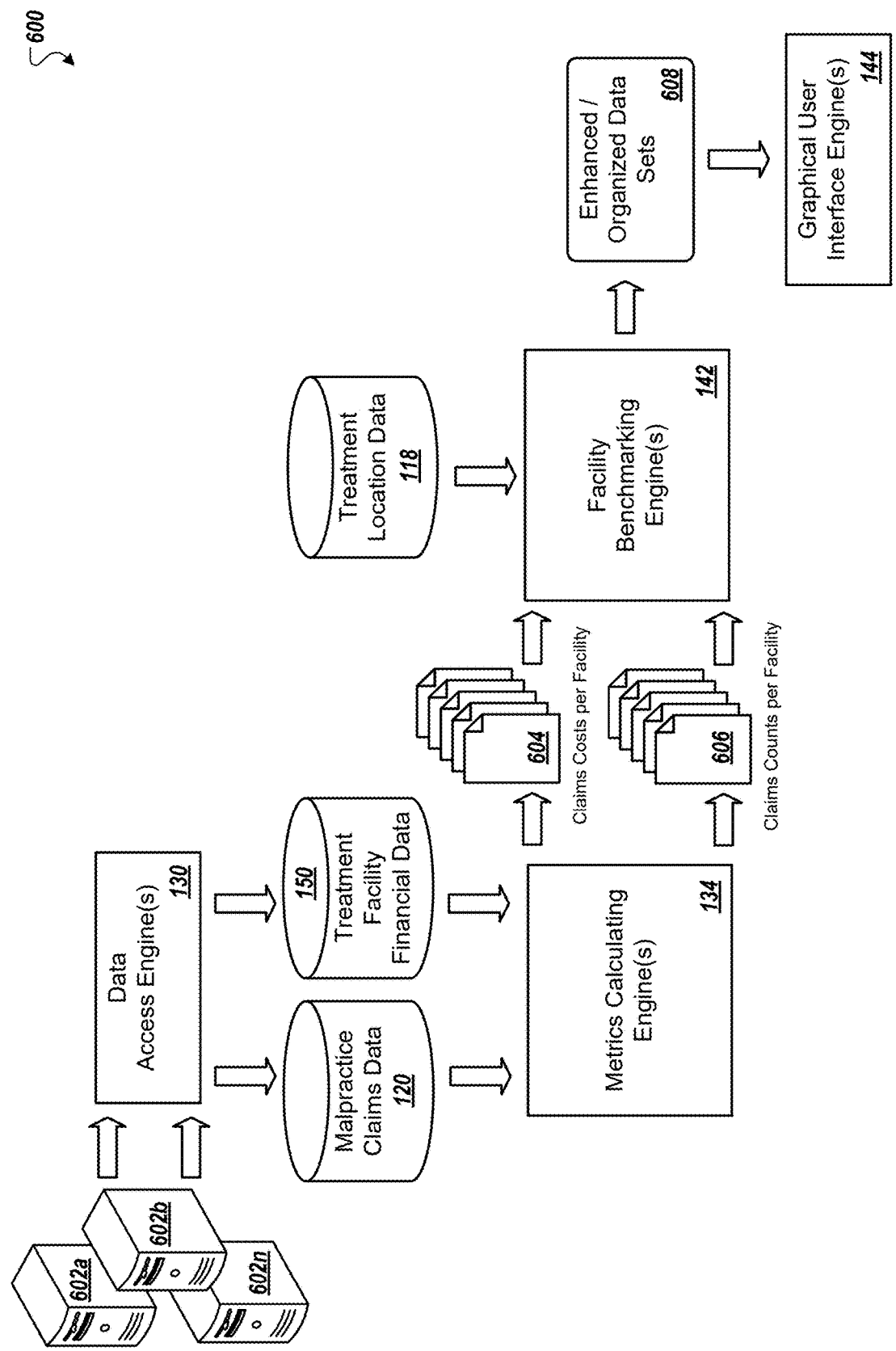
FIG. 6A is an operational flow diagram of an example process for generating benchmark metrics comparing treatment facility outcomes related to medical safety incidents.

Turning to FIG. 6A, an operational flow diagram illustrates an example process 600 for generating facility benchmarking reports and/or interactive graphical user interface displays providing comparison metrics related to malpractice claims filed against a set of healthcare facilities. The process 600, for example, may be performed by the medical liability risk and performance assessment platform 102 of FIG. 1.

In some implementations, the process 600 begins with the data access engine(s) 130 accessing, from a set of external computing systems 602, malpractice claims data 120 and treatment facility data 150. The data, for example, may be accessed through querying databases, downloading information from external servers, and/or receiving copies of data files. In some embodiments, the data access engine(s) 130 each utilizes one or more application programming interfaces (APIs) for retrieving data from at least a portion of the external computing systems 602. In other embodiments, a portion of the malpractice claims data 120 and/or the treatment facility financial data 150 may be retrieved from one or more internal storage regions.

In some implementations, the metrics calculating engine(s) 134 each calculates, from the malpractice claims data 120 and the treatment facility financial data 150, a data metrics set of claims costs per facility 604 and a data metrics set of claims counts per facility 606. Each data metrics set 604, 606 may be further refined by timeframe (e.g., per year, per quarter, per month, etc.).

In some implementations, the facility benchmarking engine(s) 142 each obtains treatment location data 118 corresponding to each facility represented in the data metric sets 604, 606. The treatment location data, for example, may include a name of each facility, location (e.g., address, county, province, state, etc.) of each facility, capacity (e.g., number of beds) of each facility, and/or a type of each facility (e.g., hospital, medical center, cancer treatment center, emergency medical care facility, surgical center, etc.).

In some implementations, the facility benchmarking engine(s) 142 each ranks, rates, classifies, and/or categorizes the healthcare facilities based at least in part on the data metrics sets 604, 606. The facility benchmarking engine(s) 142, for example, may identify mean claim costs and/or claim counts, average claim costs and/or claim counts, and/or quantiles of claim costs and/or claim counts. The facility benchmarking engine(s) 142, further to the example, may qualify each facility value using the mean(s), average(s), and/or quantiles. In some examples, the data for each facility and for each data metric set 604, 606 may be categorized based on being in a particular quantile and/or for being "better," "typical," or "worse" based on the mean(s)/average(s). Further, the facility benchmarking engine(s) 142 may rank the healthcare facilities by claim costs and/or claim counts. Additionally, the top N "best" and/or "worst" facilities may be identified, by the facility benchmarking engine(s) 142, based at least in part on the rankings. Although described as being applied across all facilities, in some embodiments, the ranking, rating, classifying, and/or categorizing may be applied to portions of similar facilities, for example based on type or capacity. In some embodiments, the facility benchmarking engine(s) 142 each produces enhanced (e.g., classified, categorized, etc.) and/or organized (e.g., ranked) data sets 608.

In some implementations, the graphical user interface engine(s) 144 each accesses the enhanced/organized data sets 608 to produce reports and/or interactive user interface displays providing comparisons between metrics of the set of facilities.

Figure 6B:
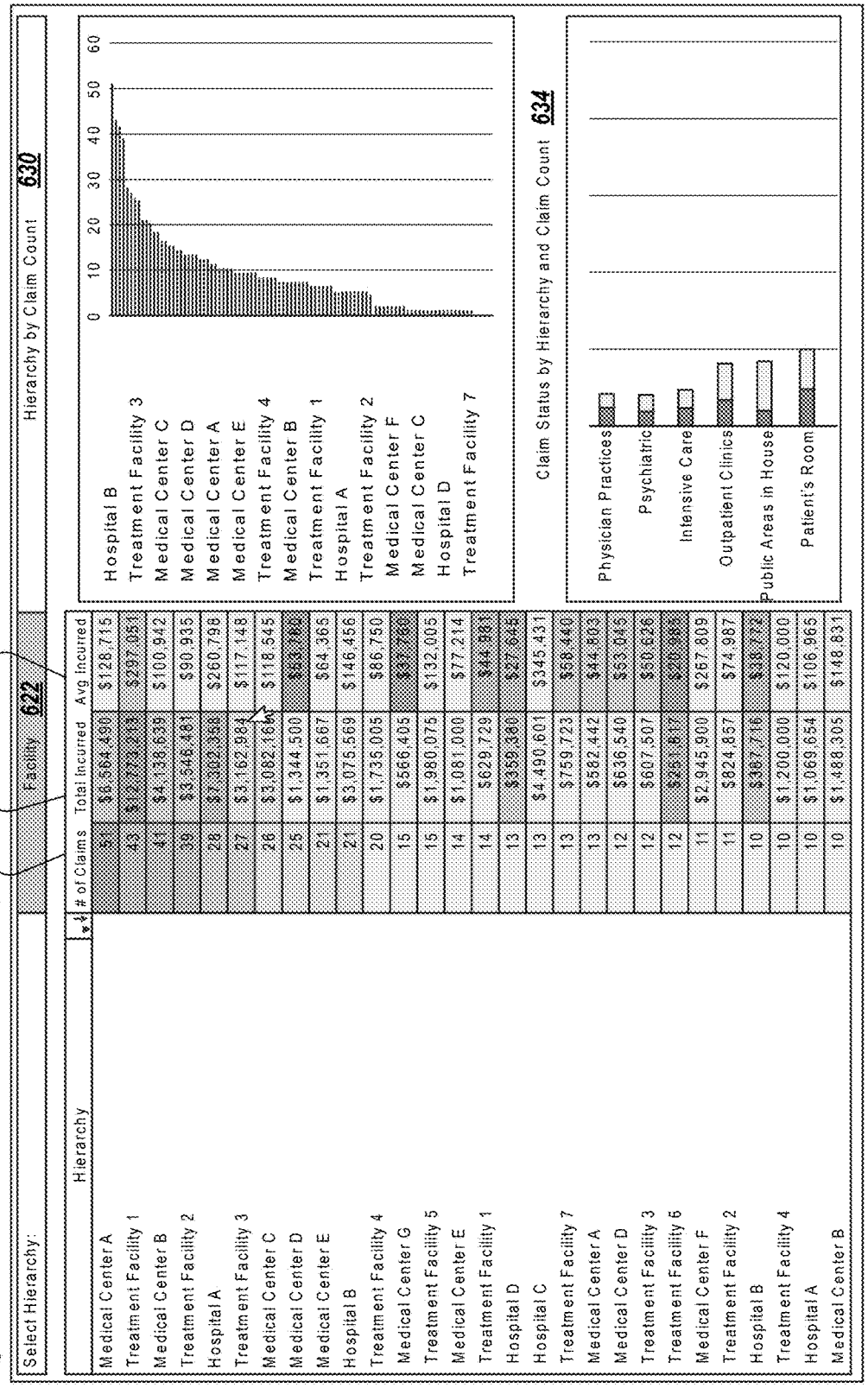
FIG. 6B and FIG. 6C illustrate an example screen shot presenting comparison metrics for a set of treatment facilities.
Figure 6C:
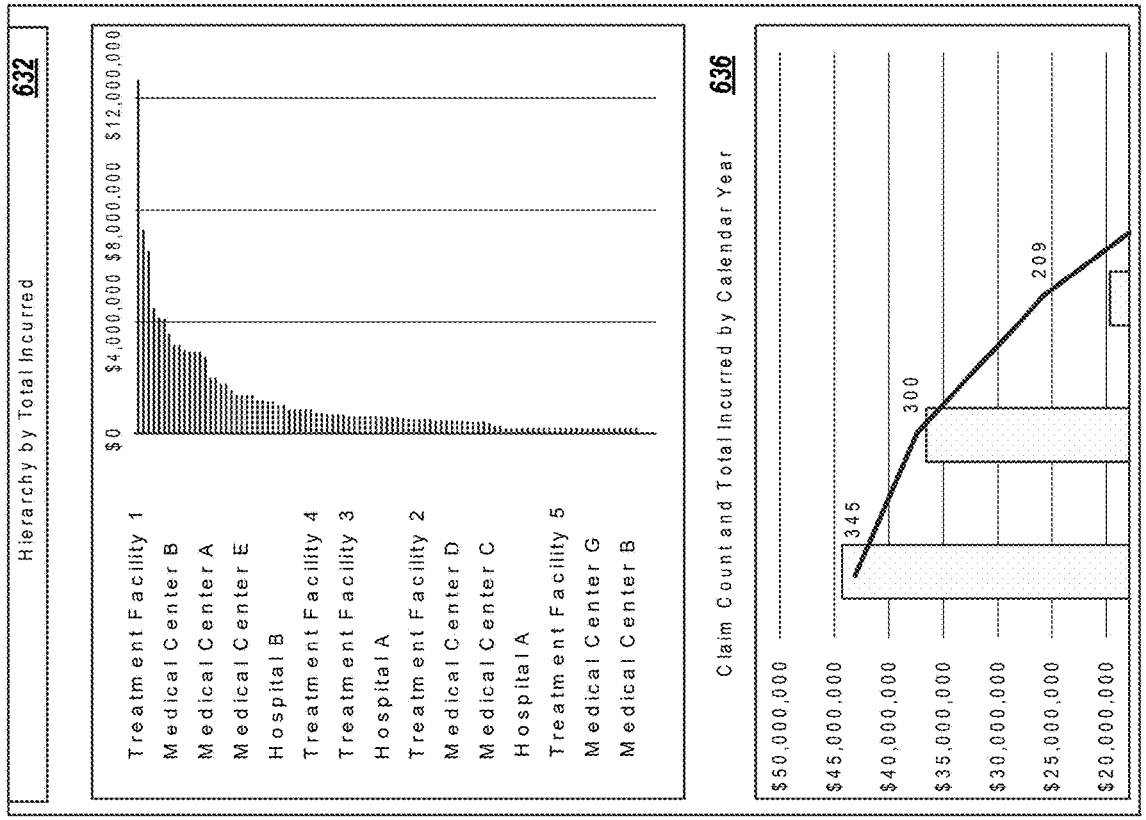

Turning to FIG. 6B and FIG. 6C, a series of portions of a screen shot illustrate an example user interface 620 for presenting comparison metrics related to medical malpractice claims. The portions of the user interface 620 illustrated in FIG. 6B and FIG. 6C, for example, may be presented side-by-side within a user interface screen. As illustrated, the comparison metrics may be presented based on a selected hierarchy 622, in the illustrated example shown on a facility level. In other examples, the metrics may be aggregated by city, county, state, metropolitan, province, or other geographic region (e.g., by zip code). In addition to the hierarchy, a target region may be identified. For example, the hospitals, treatment facilities, and medical centers illustrated in the example user interface 620 may be located in a particular target state, such as the state of Alabama presented in other user interfaces described herein.

The metrics, in some implementations, include number of claims 624, total incurred costs 626, and average incurred cost 628 by the hierarchy 622 (e.g., medical facility). As illustrated, each field of each metric column 624, 626, 628 may be color-coded (e.g., "heat mapped") from shades of green to shades of red based upon a relative difference between the respective value and an average or median value.

In some implementations, the facilities of the hierarchy 622 are ranked by total number of claims ("hierarchy by claim count") in a bar graph region 630. Further, the facilities of the hierarchy 622, in some implementations, are ranked by total cost incurred in a bar graph region 632.

In addition to data representing individual facilities of the hierarchy 622, in some implementations, a bar graph 634 illustrates a claim status by hierarchy and claim count that identifies a relative cost in gray and a relative count in red (e.g., illustrated as an initial portion of the bar, while gray extends to the right from the red).

In some implementations, a bar graph region 636 demonstrates a total number of claims and a total cost of claims across the subject facilities on a year by year basis. As illustrated, both the total count and total cost has reduced year over year for the three years presented in the bar graph region 636.

Reference has been made to illustrations representing methods and systems according to implementations of this disclosure. Aspects thereof may be implemented by computer program instructions. These computer program instructions may be provided to a processor of a general-purpose computer, special purpose computer, or other programmable data processing apparatus and/or distributed processing systems having processing circuitry, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors. The virtual processors, for example, may be part of one or more physical computing systems such as a computer farm or a cloud drive.

Aspects of the present disclosure may be implemented by software logic, including machine readable instructions or commands for execution via processing circuitry. The software logic may also be referred to, in some examples, as machine readable code, software code, or programming instructions. The software logic, in certain embodiments, may be coded in runtime-executable commands and/or compiled as a machine-executable program or file. The software logic may be programmed in and/or compiled into a variety of coding languages or formats.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations (e.g., for different object schema dimensions). The hardware logic may be synthesized on a reprogrammable computing chip such as a field programmable gate array (FPGA) or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more computing devices, such as a laptop computer, tablet computer, mobile phone or other handheld computing device, or one or more servers. Such computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device communicates, such as a server or computer. The processing circuitry and stored instructions may enable the computing device to perform, in some examples, the method 200 of FIG. 2A, the process 300 of FIG. 3A, the process 400 of FIG. 4A, and/or the process 600 of FIG. 6A.

These computer program instructions can direct a computing device or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi®, Bluetooth®, Zigbee®, or another wireless form of communication. The network, for example, may support communications between the computing devices 402 and the data access engine(s) 130 of FIG. 4A.

The computing device, in some embodiments, further includes a display controller for interfacing with a display, such as a built-in display or LCD monitor. A general purpose I/O interface of the computing device may interface with a keyboard, a hand-manipulated movement tracked I/O device (e.g., mouse, virtual reality glove, trackball, joystick, etc.), and/or touch screen panel or touch pad on or separate from the display. The display controller and display may enable presentation of the screenshots illustrated, in some examples, in FIG. 2B and FIG. 2C, FIG. 3B, FIG. 4B through FIG. 4E, and/or FIG. 6B.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the requirements of the intended back-up load to be powered.

The functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system, in some examples, may be received via direct user input and/or received remotely either in real-time or as a batch process.

Although provided for context, in other implementations, methods and logic flows described herein may be performed on modules or hardware not identical to those described. Accordingly, other implementations are within the scope that may be claimed.

In some implementations, a cloud computing environment, such as Google Cloud Platform™ or Amazon™ Web Services (AWS™), may be used perform at least portions of methods or algorithms detailed above. The processes associated with the methods described herein can be executed on a computation processor of a data center. The data center, for example, can also include an application processor that can be used as the interface with the systems described herein to receive data and output corresponding information. The cloud computing environment may also include one or more databases or other data storage, such as cloud storage and a query database. In some implementations, the cloud storage database, such as the Google™ Cloud Storage or Amazon™ Elastic File System (EFS™), may store processed and unprocessed data supplied by systems described herein. For example, the contents of the data stores 116, 118, 120, 122, 124, and/or 126 of FIG. 1, the data stores 308, 312, 316, and/or 320 of FIG. 3A, and/or the data stores 404, 406, 408, and/or 418 of FIG. 4A may be maintained in a database structure.

The systems described herein may communicate with the cloud computing environment through a secure gateway. In some implementations, the secure gateway includes a database querying interface, such as the Google BigQuery™ platform or Amazon RDS™. The data querying interface, for example, may support access by the data access engine(s) 130 to one or more data sources, such as the computing devices 602 of FIG. 6A.

The systems described herein may include one or more artificial intelligence (AI) neural networks for performing automated analysis of data. The AI neural networks, in some examples, can include a synaptic neural network, a deep neural network, a transformer neural network, and/or a generative adversarial network (GAN). The AI neural networks may be trained using one or more machine learning techniques and/or classifiers such as, in some examples, anomaly detection, clustering, and/or supervised and/or association. In one example, the AI neural networks may be developed and/or based on a bidirectional encoder representations for transformers (BERT) model by Google of Mountain View, CA.

The systems described herein may communicate with one or more foundational model systems (e.g., artificial intelligence neural networks). The foundational model system(s), in some examples, may be developed, trained, tuned, fine-tuned, and/or prompt engineered to evaluate data inputs such as the patient attributes 314, injury outcomes attributes 310, facility attributes 318 and/or medical team attributers 322 of FIG. 3A. The foundational model systems, in some examples, may include or be based off of the generative pre-trained transformer (GPT) models available via the OpenAI platform by OpenAI of San Francisco, CA (e.g., GPT-3, GPT-3.5, and/or GPT-4) and/or the generative AI models available through Azure OpenAI or Vertex AI by Google of Mountain View, CA (e.g., PaLM 2).

Certain foundational models may be fine-tuned as AI models trained for performing particular tasks required by the systems and methods described herein. Training material, for example, may be submitted to certain foundational models to adjust the training of the foundational model for performing types of analyses described herein.

Multiple foundational model systems may be applied by the systems and methods described herein depending on context. The context, for example, may include type(s) of data, type(s) of response output desired (e.g., at least one answer, at least one answer plus an explanation regarding the reasoning that lead to the answer(s), etc.). In another example, the context can include user-based context such as demographic information, entity information, and/or product information. In some embodiments, a single foundational model system may be dynamically adapted to different forms of analyses requested by the systems and methods described herein using prompt engineering.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A system for automatically deriving correlations between healthcare facility safety data and risk factors, the system comprising:
    at least one non-volatile storage region configured to store
        a plurality of facility incident records each corresponding to one of a plurality of healthcare facilities, each incident record regarding a respective liability claim or a respective safety incident, healthcare facility data comprising a plurality of healthcare facility attributes of each healthcare facility of the plurality of healthcare facilities, and a plurality of medical team records corresponding to a plurality of medical professionals each associated with one or more of the plurality of healthcare facilities; and processing circuitry configured to perform operations, comprising accessing, from the plurality of facility incident records, injury data corresponding to a plurality of injury outcomes, a plurality of injury events, and a plurality of injury causes, wherein the injury data comprises identification of a set of facility attributes of the plurality of healthcare facility attributes and a set of medical professionals of the plurality of medical professionals, automatically applying a set of standardized labels to categorize each of the plurality of injury outcomes, the plurality of injury events, and the plurality of injury causes into a respective smaller set of actionable terms consistent across the plurality of healthcare facilities, accessing, from the plurality of medical team records, medical team data corresponding to the set of medical professionals, after applying the set of standardized labels, providing, to a feature learning engine comprising one or more machine learning models, the injury data, the medical team data, and the healthcare facility data, wherein the feature learning engine is configured to identify, from the medical team data and/or the healthcare facility data, a set of risk correlation factors, wherein each risk correlation factor of the set of risk correlation factors correlates to at least one respective increased injury risk of a set of injury risks according to the injury data, and each risk correlation factor of the set of risk correlation factors identifies a respective attribute of a plurality of attributes and at least one value of the respective attribute, wherein the plurality of attributes comprises the set of facility attributes, a set of medical team attributes, and a set of patient attributes, obtaining, from the feature learning engine responsive to the providing, the set of risk correlation factors, training, using the facility attributes, the medical team data, and a portion of the set of risk correlation factors, at least one machine learning model to predict risk of safety incidents due to the portion of the set of risk correlation factors based on a collection of facility attributes and a collection of medical team data of a target medical facility.

2. The system of claim 1, wherein the operations further comprise:

accessing a plurality of incident reports; and from each report of the plurality of incident reports, extracting a set of features comprising two or more of a diagnosis, an event, a cause, or an outcome, and storing, to the at least one non-volatile storage region, the extracted set of features as a respective record of the plurality of facility incident records.

3. The system of claim 2, wherein the operations further comprise:

extracting, from each report of at least a portion of the plurality of incident reports, an identification of one or more medical professionals involved in the respective liability claim or safety incident; and for each respective report of the portion of the plurality of incident reports, identifying a respective facility incident record of the plurality of facility incident records corresponding to the respective report, and for each respective medical professional of the one or more medical professionals, from the plurality of medical team records, identifying a respective medical team record corresponding to the respective medical professional, and logically linking the respective facility incident record to the respective medical team member record.

4. The system of claim 2, wherein the operations further comprise:

extracting, from the plurality of incident reports, a set of claimants;

for each respective claimant of the set of claimants, logically linking the respective claimant to a respective patient record of a plurality of patient records; and accessing, from the plurality of patient records, claimant data comprising one or more of an age, a gender, or at least one acuity for each claimant of the set of claimants;

wherein the feature learning engine is further configured to extract the set of risk correlation factors based on the claimant data.

5. The system of claim 1, wherein training the at least one machine learning model comprises fine-tuning at least one foundational model.

6. The system of claim 1, wherein the operations further comprise:

receiving, from a remote computing device, a correlation analysis request identifying a first correlation factor and a second correlation factor of the set of risk correlation factors; and preparing, for presentation at the remote computing device, a graphical interface presenting a correlation analysis comprising identification, for each respective potential value of the first correlation factor, a level of correlation between the respective potential value of the first correlation factor and each respective potential value of the second correlation factor.

7. The system of claim 6, wherein the operations further comprise preparing, for presentation at the remote computing device, an initial graphical interface presenting a selection dialog for selecting the first correlation factor and the second correlation factor from the set of risk correlation factors.

8. The system of claim 6, wherein the identification of the level of correlation comprises a color-coding of a closeness of correlation.

9. The system of claim 6, wherein the operations further comprise, prior to preparing the graphical interface presenting the correlation analysis, removing, from the set of risk correlation factors, one or more factors outside of control by the medical facility.

10. The system of claim 9, wherein the one or more factors comprise one or more patient factors.

11. The system of claim 1, wherein the set of standardized labels comprises a set of diagnosis categories, a set of final outcome categories, and a set of event categories.

12. The system of claim 1, wherein one or more risk correlation factors of the set of risk correlation factors each represent a respective set of attributes combining two or more attribute categories of a plurality of attribute categories, wherein the plurality of attribute categories comprises a medical professional category, a facility category, and a service category.

* * * * *